US008949129B2

(12) United States Patent
Callahan et al.

(10) Patent No.: US 8,949,129 B2
(45) Date of Patent: *Feb. 3, 2015

(54) NEURAL TRANSLATOR

(71) Applicants: Michael Callahan, San Francisco, CA (US); Thomas Coleman, Champaign, IL (US)

(72) Inventors: Michael Callahan, San Francisco, CA (US); Thomas Coleman, Champaign, IL (US)

(73) Assignee: Ambient Corporation, Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/964,715

(22) Filed: Aug. 12, 2013

(65) Prior Publication Data
US 2013/0332173 A1 Dec. 12, 2013

Related U.S. Application Data

(63) Continuation of application No. 13/560,675, filed on Jul. 27, 2012, now Pat. No. 8,529,473, which is a continuation of application No. 11/825,785, filed on Jul. 9, 2007, now Pat. No. 8,251,924.

(60) Provisional application No. 60/819,050, filed on Jul. 7, 2006.

(51) Int. Cl.
G10L 13/02 (2013.01)
G10L 25/48 (2013.01)
G10L 13/04 (2013.01)
G10L 15/24 (2013.01)
A61B 5/0488 (2006.01)

(52) U.S. Cl.
CPC ............... *G10L 25/48* (2013.01); *G10L 13/043* (2013.01); *G10L 15/24* (2013.01); *A61B 5/04886* (2013.01)

USPC ........... 704/261; 704/270; 704/271; 704/259; 381/70; 381/110; 600/9; 600/23; 434/185

(58) Field of Classification Search
USPC .............. 704/200.1, 232, 236, 271, 259, 277, 704/270, 275, 223, 231, 208, 261; 381/70, 381/110; 600/9, 23, 586, 595; 434/185; 712/218, 23; 375/222; 708/207
See application file for complete search history.

(56) References Cited

U.S. PATENT DOCUMENTS

| | | | | | |
|---|---|---|---|---|---|
| 3,914,550 | A | * | 10/1975 | Cardwell, Jr. | 381/70 |
| 4,627,095 | A | * | 12/1986 | Thompson | 381/70 |
| 4,808,183 | A | * | 2/1989 | Panje | 623/9 |
| 4,901,354 | A | * | 2/1990 | Gollmar et al. | 381/110 |
| 5,072,418 | A | * | 12/1991 | Boutaud et al. | 708/207 |
| 5,536,171 | A | * | 7/1996 | Javkin et al. | 434/185 |
| 5,579,497 | A | * | 11/1996 | Ehlig et al. | 375/222 |
| 5,659,658 | A | * | 8/1997 | Vanska | 704/261 |

(Continued)

*Primary Examiner* — Vijay B Chawan
(74) *Attorney, Agent, or Firm* — McAndrews, Held & Malloy

(57) ABSTRACT

A method and apparatus are provided for processing a set of communicated signals associated with a set of muscles, such as the muscles near the larynx of the person, or any other muscles the person use to achieve a desired response. The method includes the steps of attaching a single integrated sensor, for example, near the throat of the person proximate to the larynx and detecting an electrical signal through the sensor. The method further includes the steps of extracting features from the detected electrical signal and continuously transforming them into speech sounds without the need for further modulation. The method also includes comparing the extracted features to a set of prototype features and selecting a prototype feature of the set of prototype features providing a smallest relative difference.

15 Claims, 6 Drawing Sheets

(56) References Cited

U.S. PATENT DOCUMENTS

| | | | |
|---|---|---|---|
| 5,809,462 A * | 9/1998 | Nussbaum | 704/232 |
| 5,864,806 A * | 1/1999 | Mokbel et al. | 704/234 |
| 5,867,816 A * | 2/1999 | Nussbaum | 704/232 |
| 5,907,714 A * | 5/1999 | Boutaud et al. | 712/23 |
| 6,006,175 A * | 12/1999 | Holzrichter | 704/208 |
| 6,174,278 B1 * | 1/2001 | Jaeger et al. | 600/23 |
| 6,231,500 B1 * | 5/2001 | Kehoe | 600/23 |
| 6,470,308 B1 * | 10/2002 | Ma et al. | 704/201 |
| 7,016,833 B2 * | 3/2006 | Gable et al. | 704/209 |
| 7,035,795 B2 * | 4/2006 | Burnett et al. | 704/223 |
| 7,069,177 B2 * | 6/2006 | Carley | 702/179 |
| 7,574,357 B1 * | 8/2009 | Jorgensen et al. | 704/236 |
| 7,676,372 B1 * | 3/2010 | Oba | 704/271 |
| 2006/0064037 A1 * | 3/2006 | Shalon et al. | 600/586 |
| 2007/0027676 A1 * | 2/2007 | Chambers et al. | 704/200.1 |
| 2008/0009772 A1 * | 1/2008 | Tyler et al. | 600/595 |

* cited by examiner

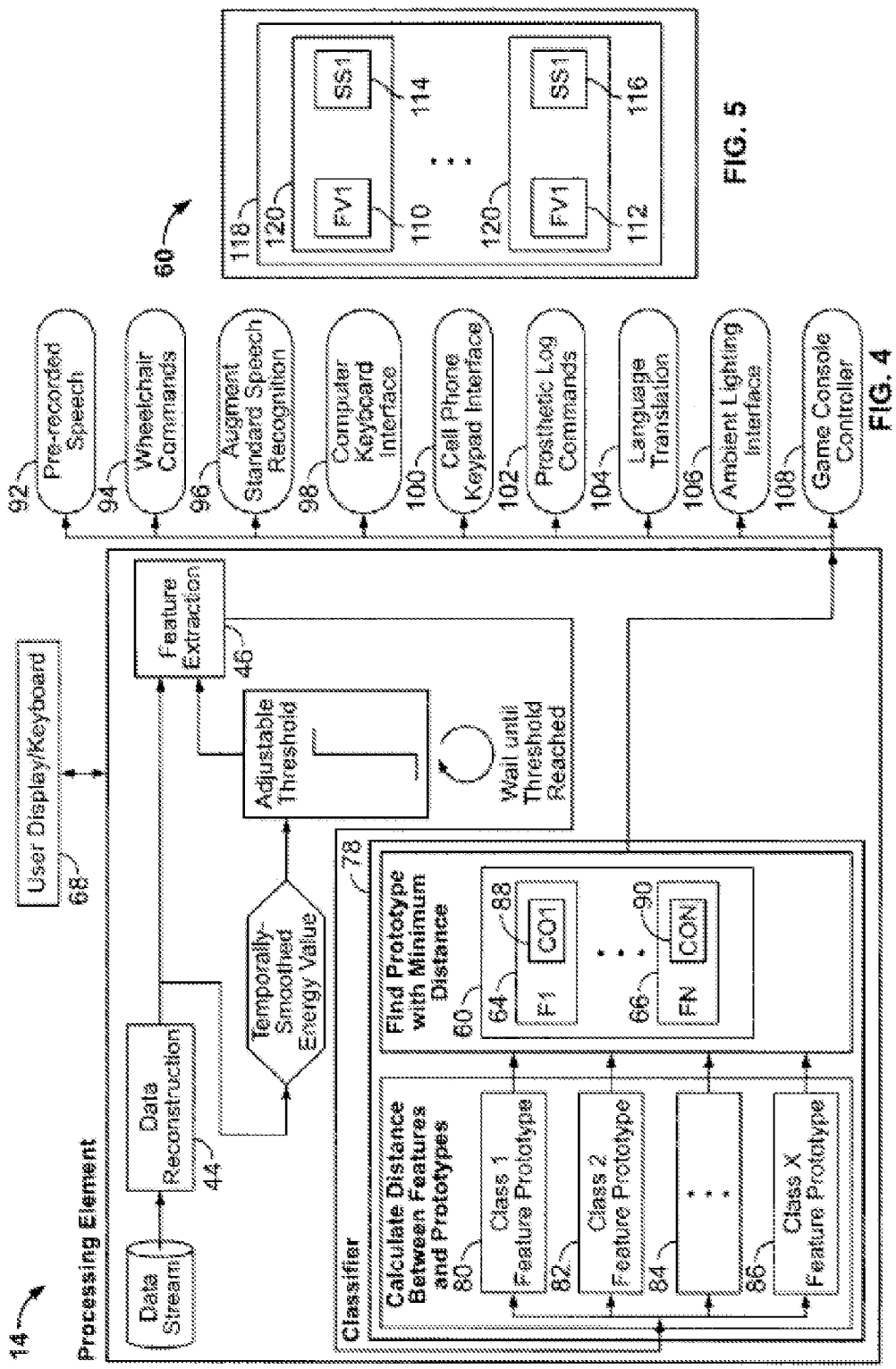

NEURAL TRANSLATOR

RELATED APPLICATIONS

This application claims priority to, and is a continuation of, U.S. application Ser. No. 13/560,675 having a filing date of Jul. 27, 2012, which is incorporated herein by reference, and which claims priority to U.S. application Ser. No. 11/825,785 (now U.S. Pat. No. 8,251,924) having a filing date of Jul. 9, 2007, which is incorporated herein by reference, and which claims priority to provisional Patent Application No. 60/819,050, filed on Jul. 7, 2006, which is also incorporated herein by reference in its entirety.

FEDERALLY SPONSORED RESEARCH OR DEVELOPMENT

[Not Applicable]

MICROFICHE/COPYRIGHT REFERENCE

[Not Applicable]

FIELD OF THE INVENTION

The field of the invention relates to the detection of nerve signals in a person and more particularly to interpretation of those signals.

BACKGROUND OF THE INVENTION

Neurological diseases contribute to 40% of the nation's disabled population. Spinal Cord Injury (SCI) affects over 450,000 individuals, with 30 new occurrences each day. 47% of Spinal Cord Injuries cause damage above the C-4 level vertebra of the spinal cord resulting in quadriplegia, like former actor Christopher Reeve. Without the use of the major appendages, patients are typically restricted to assistive movement and communication. Unfortunately, much of the assistive communication technology available to these people is unnatural or requires extensive training to use well.

Amyotrophic Lateral Sclerosis (ALS) afflicts over 30,000 people in the United States. With 5,000 new cases each year, the disease strikes without a clearly associated risk factor and little correlation to genetic inheritance. ALS inhibits the control of voluntary muscle movement by destroying motor neurons located throughout the central and peripheral nervous system. The gradual degeneration of motor neurons renders the patient unable to initiate movement of the primary extremities, including the arms, neck, and vocal cords. Acclaimed astrophysicist, Stephen Hawking has advanced stages of ALS. His monumental theories of the universe would be confined to his mind if he hadn't retained control of one finger, his only means of communicating. However, most patients lose all motor control. Despite these detrimental neuronal effects, the intellectual functionality of memory, thought, and feeling remain intact, but the patient no longer has appropriate means of communication.

Amyotrophic Lateral Sclerosis and Spinal Cord Injury (ALS/SCI) are two of the most prevalent and devastating neurological diseases. Many other diseases have similar detrimental effects: Cerebral Palsy, Aphasia, Multiple Sclerosis, Apraxia, Huntington's Disease, and Traumatic Brain Injury together afflict over 9 million people in the United States. Although the symptoms vary, the life challenges created by these diseases are comparable to SCII ALS. With loss of motor control, the production of speech can also be disabled in severe cases. Without the use of speech and mobility, neurological disease greatly diminishes quality of life, confining the patient's ideas to his or her own body. Although these individuals lack the capacity to control the airflow needed for audible sound, the use of the vocal cords can remain intact. This creates the opportunity for an interface that can bypass the communicative barriers imposed by the physical disability.

In general, three subsystems are needed to produce audible speech from a constant airflow. First, information from the brain innervates the person's diaphragm, blowing a steady air stream through the lungs. This airflow is then modulated by the opening and closing of the second subsystem, the larynx, through minute muscle movements. The third subsystem includes the mouth, lips, tongue, and nasal cavity through which the modulated airflow resonates.

The process of producing audible speech requires all components, including the diaphragm, lungs and mouth cavity to be fully functional to produce audible speech. However, inaudible' speech, which is not mouthed, is also possible using these subsystems. During silent reading, the brain selectively inhibits the full production process of speech, but still sends neurological information to the area of the larynx. Silent reading does not require regulated airflow to generate speech because it does not produce audible sound. However, the second subsystem, the larynx, can remain active.

The muscles involved in speech production can stretch or contract the vocal folds, which changes the pitch of speech and is known as phonation. The larynx receives information from the cerebral cortex of the brain (labeled "1" in FIG. 1) via the Superior Laryngeal Nerve (SLN) (labeled "2" in FIG. 1). The SLN controls distinct motor units of the Cricothyroid Muscle (CT) (labeled "3" in FIG. 1) allowing the muscle to contract or expand. Each motor unit controls approximately 20 muscle fibers which act in unison to produce the muscle movement of the larynx. Other activities involved in speech production include movement of the mouth, jaw and tongue and are controlled in a similar fashion.

The complex modulation of airflow needed to produce speech depends on the contributions of each one of these subsystems. Neurological diseases inhibit the speech 2 production process, as the loss of functionality of a single Component can render a patient unable to speak. Typically, an affected patient lacks the muscular force needed to initiate a steady flow of air. Previous technologies attempted to address this issue by emulating the activity of the dysfunctional speech production components, through devices such an electrolarynx or other voice actuator technologies. However, they still require further complex modulation capabilities which many people are no longer capable of. For example, a person both unable to initiate a steady flow of air and lacking proper tongue control would find themselves unable to communicate intelligibly using these other technologies. Despite this communicative barrier, it is possible to utilize the functionality of the remaining speech subsystems in a neural assistive communication technology. This novel technology can be utilized in a number of other useful applications, relevant to people both with and without disabilities.

BRIEF SUMMARY OF THE INVENTION

A method and apparatus are provided for processing a set of communicated signals associated with a set of muscles of a person, such as the muscles near the larynx of the person, or any other muscles the person use to achieve a desired response. The method includes the steps of attaching a single integrated sensor, for example, near the throat of the person proximate to the larynx and detecting an electrical signal through the sensor. The method further includes the steps of extracting features from the detected electrical signal and continuously transforming them into speech sounds without the need for further modulation. The method also includes comparing the extracted features to a set of prototype features and selecting a prototype feature of the set of prototype features providing a smallest relative difference.

BRIEF DESCRIPTION OF THE DRAWINGS

FIG. 4 depicts another sample processor of the system of FIG. 1 under an alternate embodiment;

FIG. 5 is a feature vector library that may be used with the system of FIG. 1;

DETAILED DESCRIPTION OF AN ILLUSTRATED EMBODIMENT

Figure 1:
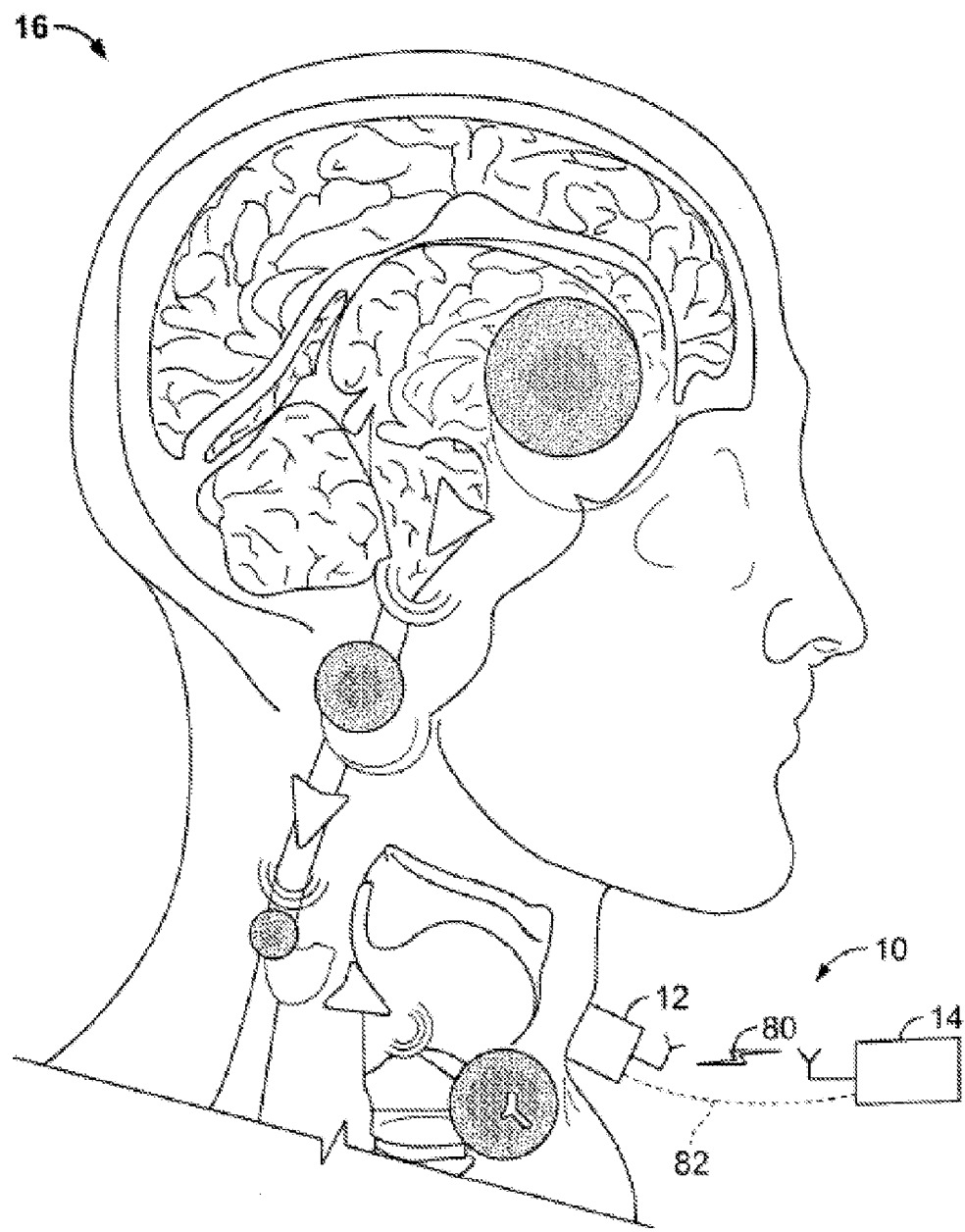
FIG. 1 depicts a system for processing neural signals shown generally in accordance with an illustrated embodiment of the invention.

FIG. 1 depicts a neural translation system 10 shown generally in accordance with an illustrated embodiment of the invention. The neural translation system 10 may be used for processing a set of communicated signals associated with a set of muscles near the larynx of a person 16.

The system 10 may be used in any number of situations where translation of signals between the person and the outside world is needed. For example, the system 10 may be used to provide a human-computer interface for communication without the need of physical motor control or speech production. Using the system 10, unpronounced speech (thoughts which are intended to be vocalized, but not actually spoken) can be translated from intercepted neurological signals. By interfacing near the source of vocal production, the system 10 has the potential to restore communication for people with speaking disabilities.

Under one illustrated embodiment, the system 10 may include a transmitting device 12 resting over the vocal cords capable of transmitting neurological information from the brain. The integrated sensor is an integral one-piece device with its own signal detection, processing, and computation mechanism. Using signal processing and pattern recognition techniques, the information from the sensor 12 can be processed to produce a desired response such as speech or commands for controlling other devices.

Figure 2:
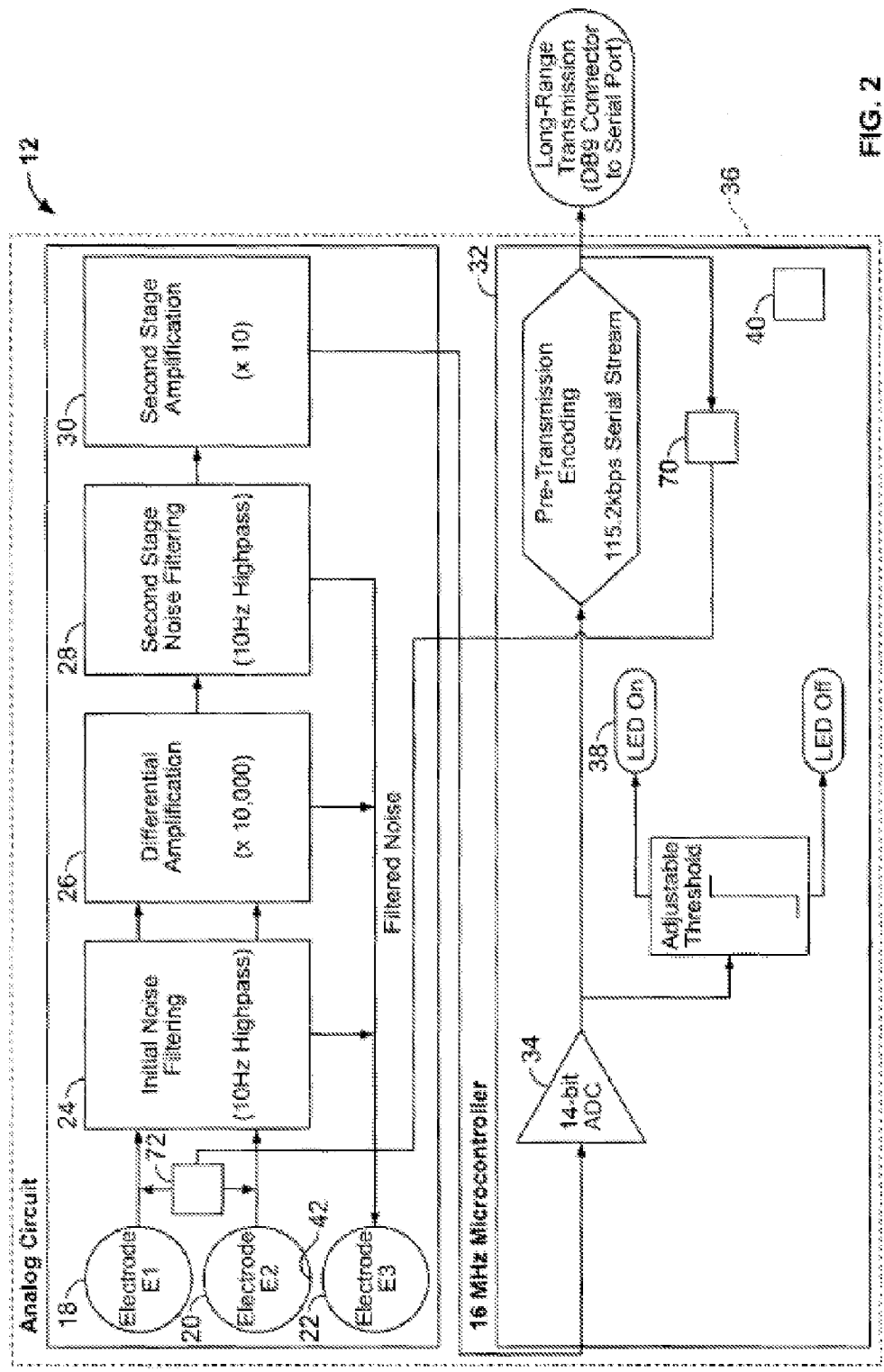
FIG. 2 depicts a sample integrated sensor of the system of FIG. 1.

Under one illustrated embodiment, the system 10 may include a wireless interface where the transmitter 12 transmits a wireless signal 130 to the processing unit 14. In other embodiments, the transmitters 12 transmits through a hardwired connection 132 between the transmitter 12 and data processing unit 14. The system 10 includes a single integrated sensor 12 attached to the neck of the person 16 and an associated processing system 14. An example embodiment of the sensor 12 is shown in FIG. 2, and consists of three conductive electrodes 18,20,22: two of them (E1 and E2) may be of the same size and reference electrode (E3) may be slightly larger.

In one embodiment, the signal from E1 and E2 first goes through a high pass filter 24 to remove low frequency (<10 Hz) bias, and is then differentially amplified using an instrumentation amplifier 26. The instrumentation amplifier also routes noise signals back into the user through the third electrode, E3.

In this embodiment, the resulting signal is further filtered for low frequency bias in a second high pass filter 28, and further amplified using a standard operational amplifier 30. A microcontroller 32 digitizes this signal into 14 bits using an analog to digital converter (ADG) 34 and splits the data point into two 7-bit packets. An additional bit is added to distinguish an upper half from a lower half of the data point (digitized sample), and each 8-bit packet is transmitted through a wired UART connection to the data processing unit 14. Additionally, the microcontroller compares each sample with a threshold to detect vocal activity. The microcontroller also activates and deactivates a feedback mechanism, such as a visual, tactile or auditory device 38.to indicate periods of activity to the user.

In this embodiment, the circuit board 36 of the sensor 12 is 13 mm wide by 15 mm long. E1, E2 are each 1 cm in diameter, and E3 is 2 cm in diameter. The size and spacing of the electrodes E1, E2, E3 has been found to be of significance. For example, to minimize discomfort to the user, the sensor 12 should be as small as possible. However, the spacing of the electrodes E1, E2 has a significant impact upon the introduction of noise through the electrodes E1, E2. Under one illustrated embodiment of the invention, the optimal spacing of the electrodes E2, E2 is one and one-half the diameter of the electrodes E1, E2. In other words, where the diameter of electrodes E1, E2 is 1 cm, the spacing is 1.5 cm. Additionally, the distance between the electrodes E1, E2, E3 and the circuit board 36 has a significant impact on noise. The electrodes are directly attached to the circuit board 36, and all components (with the exception of the electrodes and LED) are contained in a metal housing to further shield it from noise. This sensor 12 has a small power switch 40, and is attached to the user's neck using an adhesive 42 applied around the electrodes. Another embodiment could attach the sensor 12 to the user's neck with a neckband.

Figure 6:
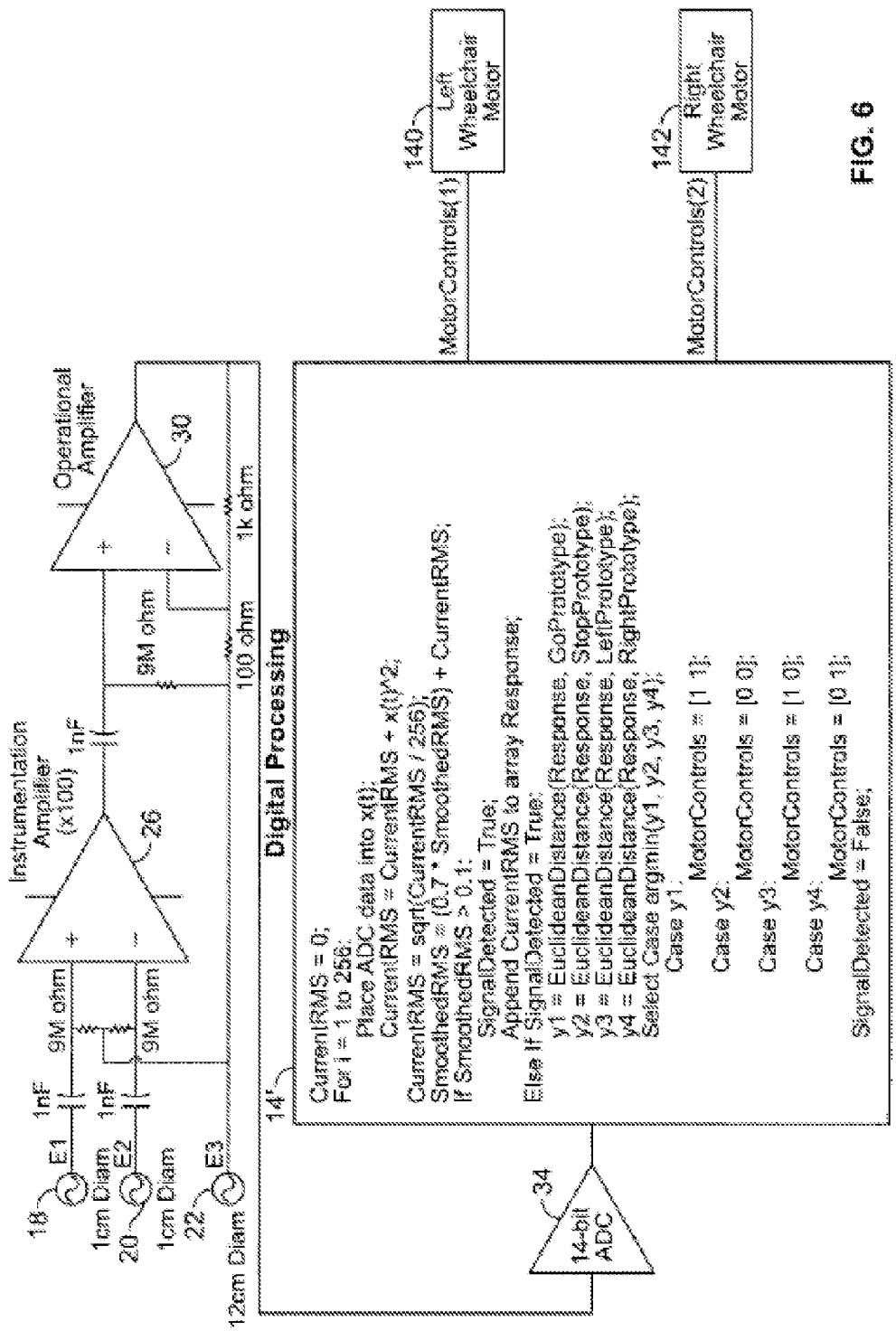
FIG. 6 is a diagram illustrating another example of the system of FIGS. 1 and 2 adapted to control a mobility device.
Figure 7:
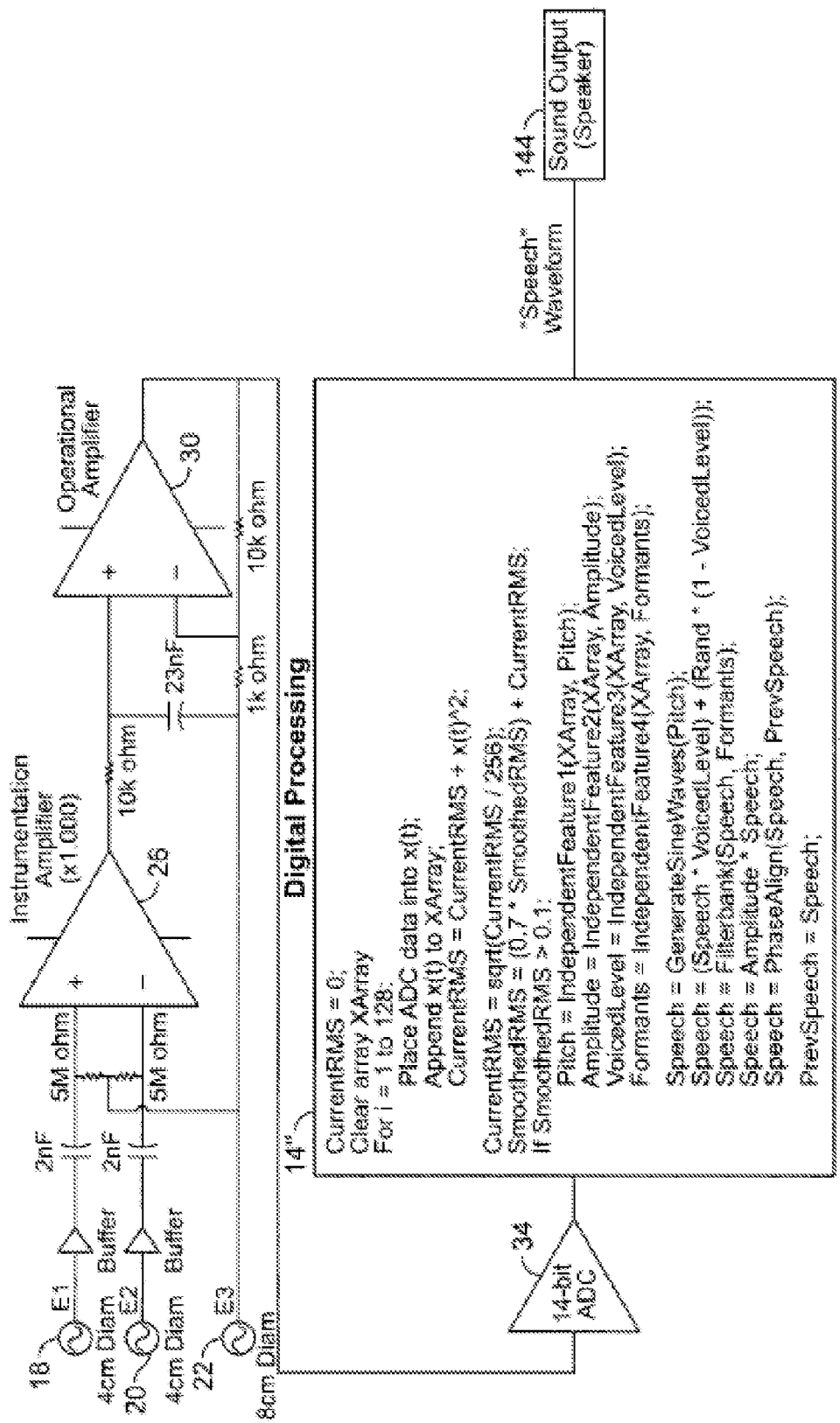
FIG. 7 is a diagram illustrating another example of the system of FIGS. 1 and 2 adapted to produce speech.

Once the digital signal reaches the processing unit 14; it is reconstructed. Reconstruction is done within the reconstruction processor 44 in this embodiment by stripping the 7 data bits from each 8-bit packet, and reassembling them in the correct order to form a 14-bit data point. Once 256 data points arrive, the data is concatenated into a 256-point data window. Additional examples of the system are illustrated in FIG. 6 and FIG. 7. In FIG. 6, the data processing unit 14 is adapted for control of wheelchair motors, and generates Left Wheelchair Motor signal 140 and Right Wheelchair Motor signal 142. In FIG. 7, the data processing unit 14 is adapted produce speech, and generates sound through Speaker 144.

In general, operation of the system 10 involves the detection of a set of communicated signals through the sensor 12 and the isolation of relevant features from those signals. As used herein, unless otherwise specifically defined, the use of the word "set" means one or more. For example, a set of communicated signals comprises a single signal and may comprise a plurality of signals. Relevant features can be detected within the communicated signals because of the number of muscles in the larynx and because different muscle groups can be activated in different ways to create different sounds. Under illustrated embodiments of the invention, the muscles of the larynx can be used to generate communicated signals (and detectable features) in ways that could generate speech or the speech sounds of a normal human voice. The main requirements are that the communicated signal detected by the sensor 12 has a unique detectable feature, be semi-consistent and have a predetermined meaning to the user.

Relevant features are extracted from the signal, and these features are either classified into a discrete category or directly transformed into a speech waveform. Classified signals can be output as speech, or undergo further processing for alternative utilization (i.e., control of devices).

The most basic type of signal distinction is the differentiation between the presence of a signal and the absence of a signal. This determination is useful for restricting further processing, as it only needs to occur when a signal is present. There are many possible features that can be used for distinction between classes, but the one preferred is the energy of a window (also known as the Euclidean vector length, ||x||, where x is the vector of points in a data window). If this value is above a threshold, then activity is present and further processing can take place. This feature, though simple and possibly suboptimal, has the important advantage of robustness to transient noise and signal artifacts.

After reconstruction of the signal, the processing unit computes the RMS value of each data window and temporally smoothes the resulting waveform. This value is compared with a threshold value within a threshold function to determine the presence of activity. If activity is present, the threshold is triggered. A set of features is extracted which represents key aspects of the corresponding detected activity. In this regard, features may be extracted in order to evaluate the activity. For example, the Fast-Fourier Transform (FFT) is a standard form of signal processing to determine the frequency content of a signal, One of the information bearing features of the FFT is the spectral envelope. This is an approximation of the overall shape of the FFT corresponding to the frequency components in the signal. This approximation can be obtained in a number of ways including a statistical mean approximation and linear predictive coding.

In addition to the spectral envelope, action potential spike distributions are another set of features that contain a significant amount of neurological information. An action potential is an electrical signal that results from the firing of a neuron. When a number of action potentials fire to control a muscle, the result is a complex waveform. Using blind-deconvolution and other techniques, it is possible to approximate the original individual motor unit action potentials (MUAPs) from the recorded activity. Features such as the distributions and amplitudes of the MUAP also contain additional information to help classify additional activity.

A number of features may be provided and evaluated using these methods, including frequency bands, wavelet coefficients, and attack and decay rates and other common time domain features. Due to the variability of the activity, it is often necessary to quantize the extracted features. Each feature can have a continuous range of values. However, for classification purposes, it is beneficial to apply a discrete range of values.

An objective metric may be necessary in order to compare features based upon their ability to classify known signals. This allows selection of the best signal features using heuristics methods or automatic feature determination. Individual features can be compared, for example, by assuming a normal distribution for each known class.

$$N_{1,2} = \frac{|\mu_1 - \mu_2|}{\sigma_1 - \sigma_2}$$

The above index, N, (where "1" and "2" are two known signal classes, e.g. "yes" and "no", and $\mu$ and $\sigma'$ may, respectively, be the mean and standard deviation of a feature value) gives a simple measure of how distinct a feature is for two known classes. In general, greater values of N indicate a feature with greater classifying potential. A similar method can be used for ranking the quality of entire feature vectors (a set of features), by replacing the means with the cluster centers and the standard deviation with the cluster dispersion.

There are two distinct ways in which the extracted features may be processed. One way is to use closed-set classification, where response classes are associated with prototype feature vectors. For a given signal, a response class is assigned by finding the prototype which best matches the signals' feature vector.

Once a set of feature values are assigned a particular meaning (class), these features can be saved as prototype features. Features can then be extracted from subsequent communicated real time signals and compared with the prototype features to determine a meaning and an action to be taken in response to a current set of communicated signals.

Machine learning techniques may be used to make the whole system 10 robust and adaptable. Optimal prototype feature vectors can be automatically adjusted for each user by maximizing the same example objective function listed previously. Response classes and their associated prototype feature vectors can be learned either in a supervised setting (where the user creates a class and teaches the system to recognize it) or in an unsupervised setting (where classes are created by the system 10 and meaning is assigned by the user). This leads to three possibilities: the system performs learning to adapt to the user, producing a complex but natural feature map relating the users' signals to their intended responses; the user learns a predefined feature map using the real-time feedback to control a simple set of features; or, both the system and the user learn simultaneously. The latter is the preferred embodiment because it combines simplicity and naturalness.

An adaptive quantization method may also be used to increase the accuracy of the system 10 as the user becomes better at controlling the device. When first introduced to the device, an adaptive quantization method may start the user with a low number of response classes that corresponds to large quantized feature step sizes. For example, a user could start with two available response classes ("Yes"/"No"). A "Yes" response would correspond to a high feature value, while a "No" response would correspond to a low feature value. As the user develops the ability to adequately control this feature between a high and low value, a new intermediate value may be introduced. With the addition of the intermediate value, the user would now have three available response classes ("Yes"/"No"/"Maybe"). Adaptively increasing the number of quantized steps would allow the user to increase the usability of the device without the inaccuracy associated with first time use.

Discrete response classes of this sort have many potential applications, especially in the area of external control. Response classes can be tied to everything from numerical digits or keyboard keys to the controls of a wheelchair. In addition, they can be combined with hierarchically structured "menus" to make the number of possible responses nearly limitless.

A second feature processing method is to use real-time feedback and continuous speech generation. Feedback is a real-time representation of key aspects of the acquired signal, and allows a user to quickly and accurately adjust their activity as it is being produced. It allows the system to change dynamically based on its outputs. Various types of stimuli such as visual, auditory, and tactile feedback help the user learn to control the features present in their signal, thereby improving the overall accuracy of the distinguished responses. The most natural medium for real-time feedback is audible sound, where the signal features are transformed into sound features.

Additional visual feedback allows the user to compare between responses and adjust accordingly. Under one illustrated embodiment, when a user produces a response, a series of colored boxes indicates the signal feature "strength." High and low signal strengths are indicated by a warm or cool color, respectively. One set of boxes may indicate the feature signal strength of the duration and the energy of the last response. Each time the user responds, the system 10 computes the overall average of all of the user's responses. Another set of boxes may keep track of these averages and gives the user an indication of consistency. Matching the colors of each set of boxes gives the user a goal which helps them gain control of the features. Once the features are mastered, the user can increase the number of responses and improve accuracy. This is similar to how actual speech production is learned using audible feedback.

Control of the signal features allows control of the audible feedback produced, including the ability to produce any sound allowable by the transformation. In the case of the continuous speech transformation, it is such that normal speech sounds are produced from the signal features. This approach bypasses many of the issues and problems associated with standard speech recognition, since it is not necessary for the system to recognize the meaning of the activity. Rather, interpretation of the speech sounds is performed by the listener. This also means that no further modulation is required for production of the speech sounds, all that is required is the presence of laryngeal neural activity in the user. As used herein, unless otherwise specifically defined, transforming the electrical signal "directly" into speech means that no further modulation of the speech sounds is required.

Listed below are two example approaches to the continuous generation of speech sounds from acquired activity. The first approach utilizes independently controllable signal features to directly control the basic underlying sound features that make up normal human speech. For example, the contraction levels of four laryngeal muscles can be extracted as features from the acquired signal from the sensor 12 using a variation of independent component analysis. Each of these contraction levels, which are independently controllable by the user, are then matched to a different speech sound feature and scaled to the same range as that speech sound feature. Typical speech sound features include the pitch, amplitude and the position of formants. The only requirement is that any normal speech sound should be reproducible from the speech sound features. It is also of note that neither the source of the acquired signals nor the sound transformation needs to be that of a human, any creature with similarly acquirable activity can be given the ability to produce normal human speech sounds. Likewise, a human can be given the capability of producing the sounds of another creature. As another example, the independently controllable signal features can be determined heuristically by presenting the user with a range of signal features and the user selecting the least correlated of those listed.

A second sample approach is to adaptively learn how to extract the actual speech sound features of the users' own voice. Audible words are first recorded along with their corresponding activity using the system 10. The recorded speech is decomposed into its speech sound features, and a supervised learning algorithm (such as a multilayer perceptron network) is trained to compute these values directly from the acquired activity. Once the transformation is suitably trained, it is no longer necessary to record audible speech. The learning algorithm directly determines the values of the speech sound features from the acquired activity, giving the user a new method of speaking. Once trained, the user can speak as they naturally would and have the same speech sounds produced.

These two example approaches are summarized as the human-learning approach and the machine-learning approach. Both can be contrasted with discrete-based methods by noticing that there are no prototypes or signal classes, instead the electrical signal and its features are directly transformed into speech sounds in real time to produce continuous speech.

Figure 3:
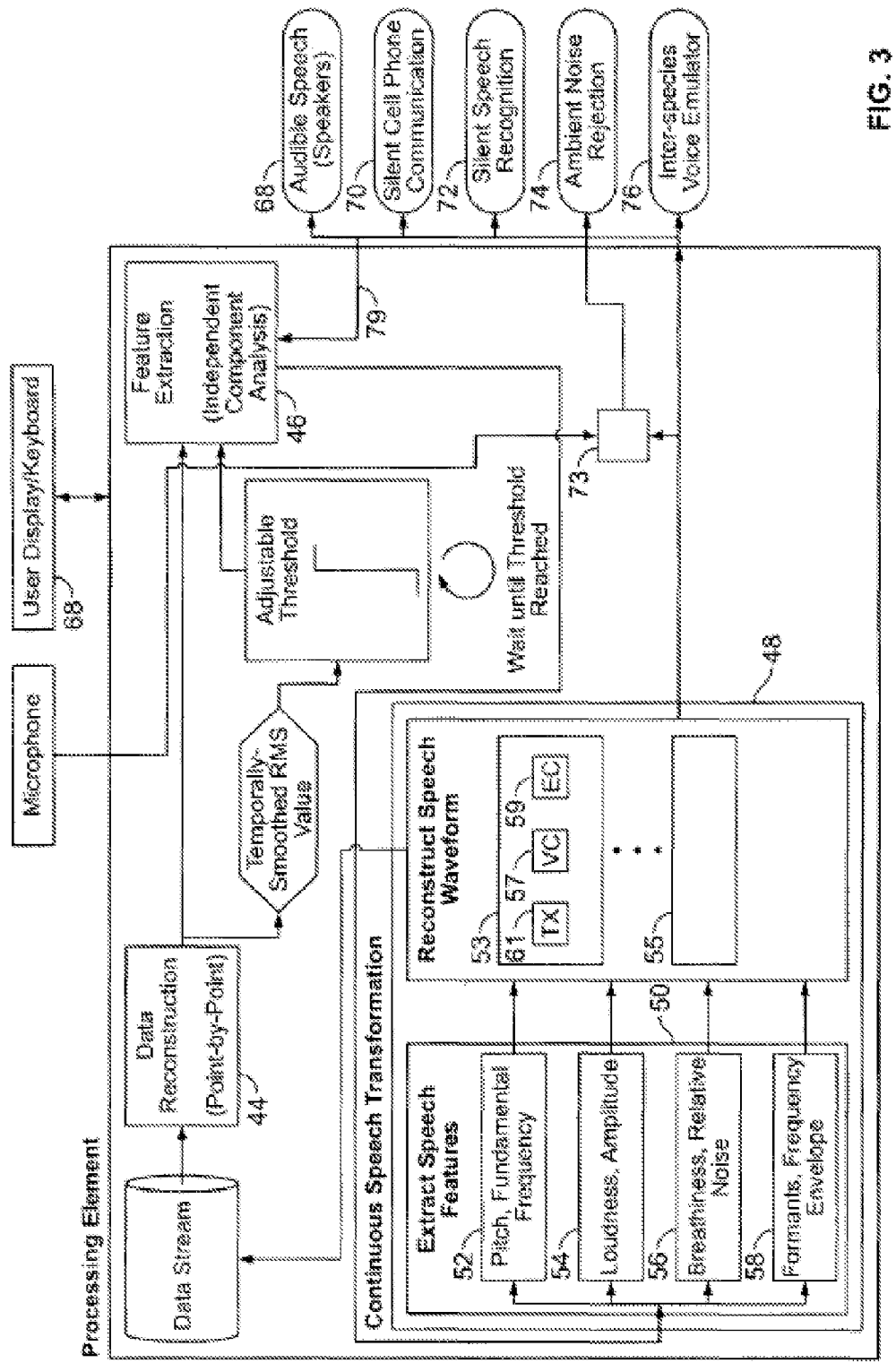
FIG. 3 depicts a sample processor of the system of FIG. 1.

FIG. 3 depicts the signal processor 14 under an illustrated embodiment related to continuous speech. In FIG. 3, a feature extraction processor 46 may extract features from the data stream when the data stream is above the threshold value.— Features extracted by the feature extraction processor 46 may include one or more of the frequency bands, the wavelet coefficients and/or various common time domain features present within the speech related to activity near the larynx. The extracted features may be transferred to a continuous speech transformation processor 48. Within the speech transformation processor 48, a speech features processor 50 may correlate and process the extracted features to generate speech.

Under one illustrated embodiment, the extracted features are related to a set of voice characteristics. The set of voice characteristics may be defined, as above, by the quantities of the pitch (e.g., the fundamental frequency of the pitch), the loudness (i.e., the amplitude of the sound), the breathiness (e.g., the voiced/unvoiced levels) and formants (e.g., the frequency envelope of the sound). For example, a first extracted feature 52 is related to pitch, a second extracted characteristic 54 is related to loudness, a third characteristic 56 is related to breathiness and a fourth characteristic 58 is related to formants of speech. The set of features are scaled as appropriate.

To generate speech using. the above example speech features 53, the fundamental frequency is first used to generate sine waves 61 of that frequency and its harmonics. The sine waves are then scaled in amplitude according to the loudness value 57, and the result is linearly combined with random values. in a ratio determined by the breathiness value 59. Finally, the resulting waveform is placed through a filter bank described by the formant value. The end result is speech generated directly from the sensor 12.

One embodiment could use this generated speech in a' speech-to-text based application 55, which would extract some basic meaning from the speech sounds for further processing.

Under another alternate embodiment, the system 10. may be used for silent communication through a electronic communication device (such as a cellular phone). In this case, the feature vectors may be correlated to sound segments within files 64, 66 and provided as an audio input to a silent cell phone communication interface 70 either directly or through the use of a wireless protocol, such as Bluetooth or Zigbee. The audio from the other party of a cell phone call may be provided to the user through a conventional speaker.

Under another embodiment, communication through a communication device may occur without the use of a speaker. In this case, the audio from the other party to the cell phone conversation is converted to an electrical signal which is then applied to the larynx of the user.

In order to provide the electrical input to the larynx of the user, the audio to the other party may be provided as an input to the feature extraction processor 46 through a separate connection 77. A set of feature vectors 52, 54, 56, 58 is created as above. Matching of the set of feature vectors with a file 64, 66 may be made based upon the smallest relative distance as discussed above to identify a set of words spoken by the other party to the conversation.

Once the file 64, 66 is identified for each data segment, the contents of the file 64, 66 are retrieved. The contents of the file 64, 66 may be an electrical profile that would generate equivalent activity of the vocal aperture of the user. The electrical profile is provided as a set of inputs to drivers 70, 72 and, in turn, to the electrodes 18, 20 and larynx of the person 16.

In effect, the electrical profile causes the user's larynx to contract as if the user were forming words. Since the user is familiar with the words being formed, the effect is that of words being formed and would be understood based upon the effect produced in the larynx of the user. In effect, the user would feel as if someone else were forming words in his/her larynx.

In another illustrated embodiment, the output 72 of the system may be a silent form of speech recognition. In this case, the matched files 64, 66 may be text segments that are concatenated as recognized text on the output 72 of the system 10.

In another illustrated embodiment, the output 74 of the system 10 may be used in conjunction with other sound detection equipment to cancel ambient noise. In this case, the matched files 64, 66 identify speech segments. Ambient noise (plus speech from the user) is detected by a microphone which acquires an audible signal. The identified speech segments are then subtracted from the ambient noise within a summer 73. The difference is pure ambient noise that is then output as an ambient noise rejection signal 74, thereby eliminating unwanted ambient noise from speech.

In another illustrated embodiment, the output 76 may be used as an inter-species voice emulator. For example, it is known that some primates (e.g., chimps) can learn sign language, but cannot speak like a human because the required structure is not present in the larynx of the primate. However, since primates can be taught sign language, it is also possible that a primate could be taught to use their larynx to communicate in an audible, human sounding manner. In this case, the system 10 would function as an interspecies voice emulator.

FIG. 4 depicts a processing system 14 under another illustrated embodiment. In this case, the feature extraction processor 46 extracts a set of features from the data stream and sends the features to a classifier processor 78. The classifier processor 78 processes the features to identify a number of RMS peaks by magnitude and location. The data associated with the RMS peaks is extracted and used to classify the extracted features into one or more feature vectors 80, 82, 84, 86 associated with specific types of communicated signals (e.g., "Go Forward", "Stop", "Go Left", "Go Right", etc.). The classification processor 78, which compares each feature vector 80, 82, 84, 86 with a set of stored prototype feature vectors 64, 66 corresponding to the set of classifications and best possible responses. The best matching response may be chosen by the comparison processor 60 based on a Euclidean or some other distance metric, and the selected file 64, 66 is used to provide a predetermined output 88, 90.

Under one illustrated embodiment of the invention (FIG. 5), one or more libraries 118 of predetermined speech elements of the user 16 are provided within the comparison processor 60 to recreate the normal voice of the user. In this case, the normal speech of the user is captured and recorded both as feature vectors 110, 112 and also as corresponding audio samples 114, 116. The feature vectors 110, 11,2 may be collected as discussed above. The audio samples 114, 116 may be collected through a microphone and converted into the appropriate digital format (e.g., a WAV file). The feature vector 110, 112 and respective audio sample 114, 116 may be saved in a set of respective files 120, 122.

In this illustrated embodiment, the electrical signals detected through the sensor 12 from the user are converted into the normal speech in the voice of the user by matching the feature vectors of the real time electrical signals with the prototype feature vectors 110, 112 of the appropriate library file 120, 122. Corresponding audio signals 114, 116 are provided as outputs in response to matched feature vectors. The audio signal 114, 116 in the form of pre-recorded speech may be provided as an output to a speaker through a pre-recorded speech interface 92 or as an input to a cell phone or some other form of communication channel.

By using the system 10 in this manner, a user standing in a very noisy environment may engage in a telephone conversation without the noise from the environment interfering with the conversation through the communication channel. Alternatively, the user may simply form the words in his/her larynx without making any sound so as to privately engage in a cell phone conversation in a very public space.

In another illustrated embodiment, the library 118 contains audible speech segments 114, 116 in an idealized form. This can be of benefit for a user who cannot speak in an intelligible manner. In this case, the feature vectors 110, 112 are recorded and associated with the idealized words using the classification 'process as discussed above. In cases of severe disability, the user may need to use the user display/keyboard 68 to associate the recorded feature vectors 110, 112 with the idealized speech segments 114, 116. When a real time feature vector is matched with a recorded prototype feature vector, the idealized speech segments are provided as an output through an augment standard speech recognition output 96.

In another illustrated embodiment, the library 118 contains motor commands 114, 116 that are provided to a mobility vehicle (such as a powered wheelchair) through a mobility vehicle interface 94. This can be of benefit for a user who may be a quadriplegic or otherwise cannot move his/her arms. In this case, the user may select wheelchair commands by some unique communicated signal (e.g., activating his larynx to voice a command string such as the words "wheelchair forward"). As above, the feature vectors 110, 112 may be recorded from the user and associated with the commands using the classification process as discussed above. In cases of severe disability, the user may need to use the user display/keyboard 68 to associate the recorded feature vectors 110, 112 with the commands 114, 116. When a real time feature vector is matched with a recorded prototype feature vector, the corresponding wheelchair motor command is provided as an output through the wheelchair interface 94.

In another illustrated embodiment, the library 118 contains computer mouse (cursor) and mouse switch commands 114, 116 through a computer interface 98. This can be of benefit for a user who may be a quadriplegic or otherwise cannot move his/her arms. In this case, the user may select computer command by some unique communicated signal (e.g., activating his larynx to otherwise voice a command string such as the words "mouse click"). As above, the feature vectors 110, 112 may be recorded from the user and associated with the commands using the classification process as discussed above. In cases of severe disability, the user may need to use the user display/keyboard 68 to associate the recorded feature vectors 110, 112 with the commands 114, 116. When a real time feature vector is matched with a recorded prototype feature vector, the corresponding computer command is provided as an output through a computer interface 98.

In another illustrated embodiment, the library 118 contains commands 114, 116 for a communication device (such as a cellular phone). This can be of benefit for a user who may be a quadriplegic or otherwise cannot move his/her arms. In this case, the cell phone commands may be in the form of a keypad interface, or voice commands through a voice channel to a voice processor within the telephone infrastructure. The system 10 may be provided with a plug in connection to a voice channel and/or to a processor of the cell phone through a cell phone interface 100. The user may select cell phone commands by some unique communicated signal (e.g., activating his larynx "to voice a command string such as the words "phone dial"). As above, the feature vectors 110, 112 may be recorded from the user and associated with the commands using the classification process as discussed above. In cases of severe disability, the user may need to use the user display/keyboard 68 to associate the recorded feature vectors 110, 112 with the cell phone commands 114, 116. When a real time feature vector is matched with a recorded prototype feature vector, the cell phone commands are provided as an output through the cell phone interface 100.

In another illustrated embodiment, the library 118 contains prosthetic commands 114, 116. This can be of benefit for a user who may be a quadriplegic or otherwise cannot move his/her arms. The user may select prosthetic command by some unique communicated signal (e.g., activating his larynx to voice a command string such as the words "arm bend"). As above, the feature vectors 110, 112 may be recorded from the user and associated with the commands using the classification process as discussed above. In cases of severe disability, the user may need to use the user display/keyboard 68 to associate the recorded feature vectors 110, 112 with the prosthetic commands 114, 116. Selected prosthetic commands may be provided to the prosthetic through a prosthetic interface 102.

In another illustrated embodiment, the library 118 contains translated words and phrases 114, 116. This can be of benefit for a user who needs to be able to converse in some other language through a language translation interface 104. The user may select language translation by some unique communicated signal (e.g., activating his larynx to voice a command string such as the words "voice translation"). As above, the feature vectors 110, 112 may be recorded from the user and associated with the translated words and phrases using the classification process as discussed above. When a real time prototype feature vector is matched with a recorded feature vector, the translated word or phrase is provided as an output through language translation interface 104.

In another illustrated embodiment, the library 118 contains environmental (e.g., ambient lighting, air conditioning, etc.) control commands 114, 116. This can be of benefit for a user who needs to be able to control his environment through a environmental control interface 106. The user may select environmental control by some unique communicated signal (e.g., activating his larynx to voice a command string such as the words "temperature increase"). As above, the feature vectors 110, 112 may be recorded from the user and associated with the environment using the classification process as discussed above. In cases of severe disability, the user may need to use the user display/keyboard 468 to associate the recorded feature vectors 110, 112 with the environmental control commands 114, 116. When a real time feature vector is matched with a recorded prototype feature vector, the corresponding environmental control is provided as an output through the environmental control interface 106.

In another illustrated embodiment, the library 118 contains game console control commands 114, 116. This can be of benefit for a user who needs to be able to control a game console through a game console controller 108. The user may select game console by some unique communicated signal (e.g., activating his larynx to voice a command string such as the words "Control pad up."). As above, the feature vectors 110, 112 may be recorded from the user and associated with the game console control commands using the classification process as discussed above. In cases of severe disability, the user may need to use the display/keyboard 68 to associate the recorded feature vectors 110, 112 with the game console control commands 114, 116. When a real time feature vector is matched with a recorded feature vector, the corresponding game control command is provided as an output through the game control interface 108.

The reliability of the system 10 is greatly enhanced by use of the integrated sensor 12, including the processor 14. The integration of the sensor 12 enables data collection to be performed much more efficiently and reliably than was previously possible, and allows the data processor 14 to operate on the signal of a single sensor where multiple sensors were previously required in other devices. It also enables portability and mobility, two practical concerns which were not previously addressed. The sensor 12 contains a mix of analog and digital circuitry, both of which are placed extremely close to the electrodes. Minimizing the length of all analog wires and traces allows the sensor 12 to remain extremely small and sensitive while picking up a minimal amount of external noise. A microcontroller digitizes this signal and prepares it for reliable transmission over a longer distance, which can occur through a cable or a wireless connection. Further processing is application-dependent, but shares the general requirements outlined above. It should be noted that possible embodiments can have different values, algorithms, and form factors from what was shown, while still serving the same purpose.

The system 10 offers a number of advantages over prior systems. For example, the system 10 functions to provide augmentative communication for the disabled, using discrete classification (including phrase-based recognition) of activity from the user. The system 10 can accomplish this objective by comparing signal features to a set of stored prototypes, to provide a limited form of communication made possible for those who otherwise would have no way of communicating.

It should be specifically noted in this regard that the system 10 is not limited to articulate words, syllables or phonemes, but may also be extended to activity that would otherwise produce unintelligible as speech or even no sound at all. The only requirement in this case is' that the electrical signal detected through the sensor 12 need to be distinguishable based upon some extractable feature incorporated into the prototype feature vector.

The system 10 may also provide augmentative communication for the people with disabilities, using continuous speech synthesis. By directly transforming signal features into speech features, a virtually unlimited form of communication is possible for those who otherwise would lack the sound modulation capabilities to produce intelligible speech.

The system 10 can also provide silent communication using discrete classification (including phrase-based recognition). By comparing a signal to a set of stored prototypes, a limited form of silent communication is possible.

The system 10 can also augment speech recognition. In this case, standard speech recognition techniques can be improved by the processing and classification techniques described above.

The system 10 can also provide a computer interface. In this case, signal processing can be done in such a way as to emulate and augment standard computer inputs, such as a mouse and/or keyboard.

The system 10 can also function as an electronic communication device interface. In this case, signal processing can be done in such a way as to emulate and augment standard cell phone inputs, such as voice commands and/or a keypad.

The system 10 can also provide noise reduction for communication equipment. By discerning which sounds were made by the user and which were not, a form of noise rejection can be implemented.

The system 10 can provide inter-species voice emulation. One species can be given the vocal capabilities of another species, enabling a possible form of inter-species communication.

The system 10 can provide universal language translation. Signal processing can be integrated into a larger system to allow recognized speech to be transformed into another language.

The system 10 can provide bidirectional communication using muscle stimulation. The process flow of the invention can be reversed such that external electrical stimulation allows communication to a user.

The system 10 can provide mobility, for example, to people with disabilities (including wheelchair control). By comparing signal features to a set of stored command prototypes, a self-propelled mobility vehicle can be controlled by the invention.

The system 10 can provide prosthetics control. By comparing signal features to a set of stored command prototypes, prosthetics can be controlled by the invention.

The system 10 can provide environmental control. By comparing signal features to a set of stored command prototypes, aspects of a users' environment can be controlled by the invention.

The system 10 can be used for video game control. Signal processing can be done in such a way as to emulate and augment standard video game inputs, including joysticks, controllers, gamepads, and keyboards.

A specific embodiment of the method and apparatus for processing neural signals has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. A method of processing a set of communicated signals, said method comprising:
attaching a sensor near an area of a user's body associated with speech production;
detecting an electrical signal from the user's nervous system through the sensor;
processing the electrical signal to extract a set of features of the signal; and
comparing the set of features with a set of prototype features, wherein the set of prototype features corresponds to at least one of multiple response classes.

2. The method of claim 1, wherein the multiple response classes include an affirmative response class and a negative response class.

3. The method of claim 1, wherein the area of the user's body associated with speech production is the user's brain.

4. The method of claim 1, further comprising:
selecting a prototype from the set of prototype features with a minimum difference between the prototype feature and the set of features of the signal.

5. The method of claim 4, further comprising:
controlling a computing device using a command associated with the prototype.

6. The method of claim 4, further comprising:
controlling an electronic communication device using a command associated with the prototype.

7. The method of claim 1, further comprising:
wirelessly transmitting the electrical signal to a signal processing unit.

8. An apparatus for processing a set of communicated signals comprising:
a sensor configurable to be attached near an area of a user's body associated with speech production;
an electrode configurable to detect an electrical signal from the user's nervous system through the sensor;
an extraction processor configurable to extract a set of features from the detected electrical signal; and
a classification processor configurable to compare the extracted features with a set of prototype features, wherein the set of prototype features corresponds to at least one of multiple response classes.

9. The apparatus of claim 8, wherein the multiple response classes include an affirmative response class and a negative response class.

10. The apparatus of claim 8, wherein the area of the user's body associated with speech production is the user's brain.

11. The apparatus of claim 8, further comprising:
a comparator configurable to select a prototype feature of the set of prototype features with the smallest relative difference.

12. The apparatus of claim 11, wherein a command associated with the prototype is configurable to control a computing device.

13. The apparatus of claim 11, wherein a command associated with the prototype is configurable to control an electronic communication device.

14. The apparatus of claim 8, further comprising:
an analog to digital converter disposed within the sensor and configurable to convert the detected electrical signal into an equivalent digital signal.

15. The apparatus of claim 14, further comprising:
a wireless transmitter configurable to wirelessly transmit the digital signal to a signal processing unit.

* * * * *